(12) United States Patent
Marin et al.

(10) Patent No.: US 10,717,945 B2
(45) Date of Patent: Jul. 21, 2020

(54) MIXTURE COMPRISING AT LEAST DIHYDRO-5-PENTYL-2(3H)-FURANONE AND 2,4-DIMETHYL-4-PHENYLTETRA-HYDROFURAN AND USE THEREOF FOR MASKING UNPLEASANT ODOURS

(71) Applicant: EXPRESSIONS PARFUMEES, Grasse (FR)

(72) Inventors: Christophe Marin, Nice (FR); Stéphane Coez, Peymeinade (FR); Jennifer Buzzi, Grasse (FR); Christophe Deroo, Antibes (FR)

(73) Assignee: EXPRESSIONS PARFUMEES, Grasse (FR)

( * ) Notice: Subject to any disclaimer, the term of this patent is extended or adjusted under 35 U.S.C. 154(b) by 0 days.

(21) Appl. No.: 16/310,246

(22) PCT Filed: Jun. 14, 2017

(86) PCT No.: PCT/FR2017/051526
§ 371 (c)(1),
(2) Date: Dec. 14, 2018

(87) PCT Pub. No.: WO2017/216478
PCT Pub. Date: Dec. 21, 2017

(65) Prior Publication Data
US 2019/0330561 A1    Oct. 31, 2019

(30) Foreign Application Priority Data
Jun. 16, 2016 (FR) .................................. 16 55608

(51) Int. Cl.
| | | |
|---|---|---|
| *A61K 8/18* | (2006.01) | |
| *A61K 8/00* | (2006.01) | |
| *A61Q 13/00* | (2006.01) | |
| *C11B 9/00* | (2006.01) | |
| *A61K 8/35* | (2006.01) | |
| *A61K 8/37* | (2006.01) | |
| *A61K 8/49* | (2006.01) | |

(52) U.S. Cl.
CPC .............. *C11B 9/0076* (2013.01); *A61K 8/35* (2013.01); *A61K 8/37* (2013.01); *A61K 8/4973* (2013.01); *A61Q 13/00* (2013.01); *A61K 2800/5922* (2013.01)

(58) Field of Classification Search
CPC ........... C11B 9/0076; A61K 8/35; A61K 8/37; A61K 8/4973; A61K 2800/5922; A61Q 13/00
USPC ................................................... 512/11, 8, 1
See application file for complete search history.

(56) References Cited

FOREIGN PATENT DOCUMENTS

| | | | |
|---|---|---|---|
| CN | 1948447 A | 4/2007 | |
| EP | 1737937 B1 | 6/2013 | |
| GB | 2528480 A | 1/2016 | |
| WO | 2008104352 A2 | 9/2008 | |
| WO | WO-2008104352 A2 * | 9/2008 | ......... C11D 3/38627 |

OTHER PUBLICATIONS

International Search Report from corresponding International Application No. PCT/FR2017/051526, dated Sep. 29, 2017, pp. 1-3, European Patent Office, Rijswijk, The Netherlands.

* cited by examiner

*Primary Examiner* — Jessica Whiteley
(74) *Attorney, Agent, or Firm* — Hauptman Ham, LLP

(57) ABSTRACT

The present invention relates to an odoriferous mixture with improved intensity and longevity, capable of masking bad odours, said mixture comprising at least dihydro-5-pentyl-2(3H)-furanone at a percentage between 20 and 80% by weight and 2,4-dimethyl-4-phenyltetrahydrofuran at a percentage between 20 and 80% by weight, the percentages by weight being relative to the total weight of said mixture. The invention also relates to the cosmetic, detergent or scented products comprising said mixture.

20 Claims, 5 Drawing Sheets

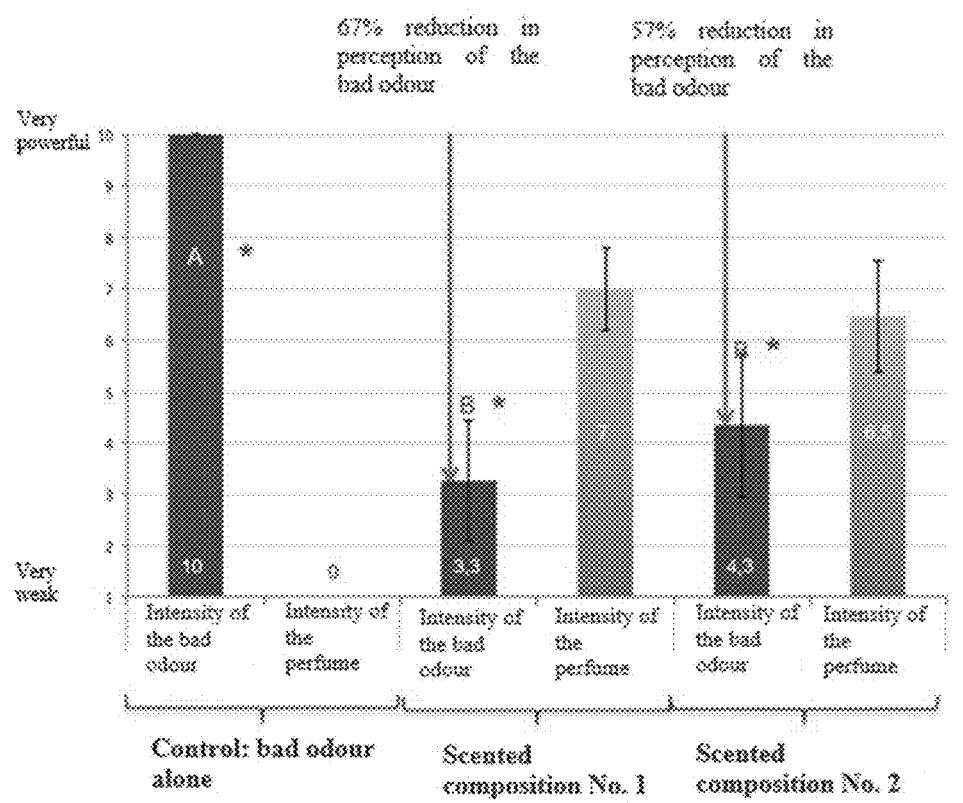
Figure 1 : Results of the sensory evaluation against the bad tobacco odour

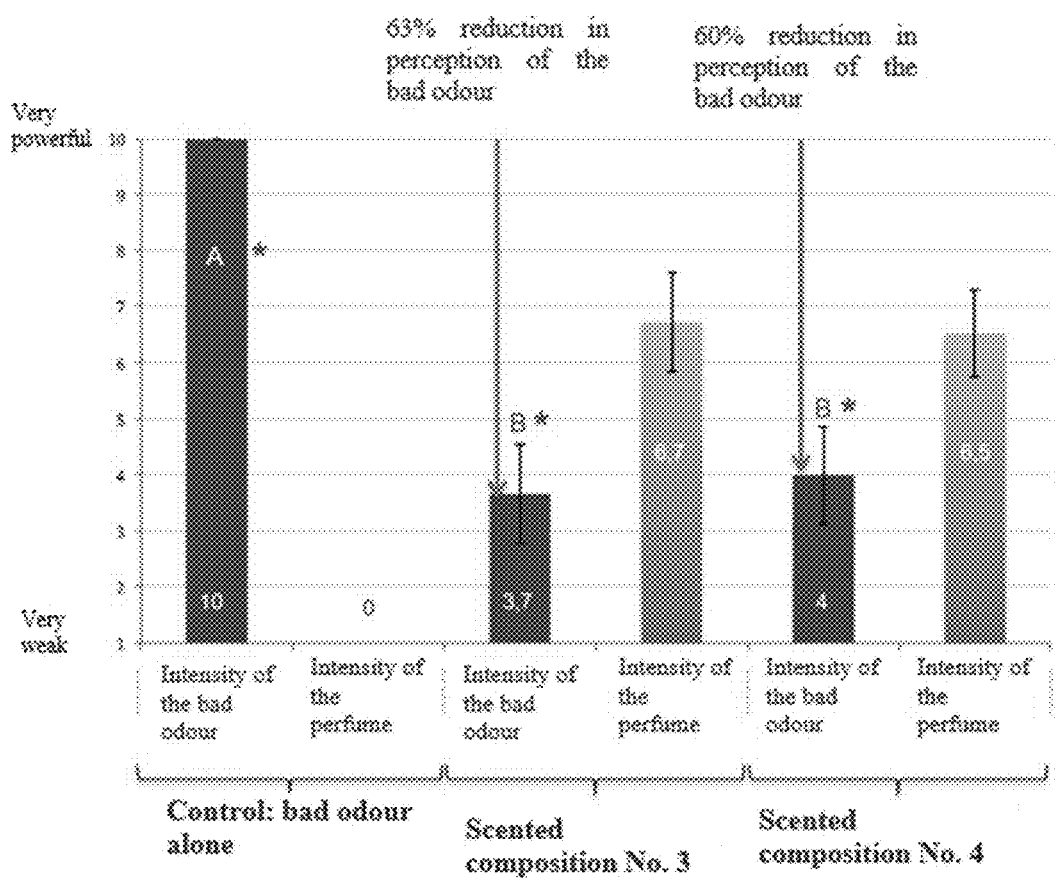
Figure 2 : Results of the sensory evaluation against the bad kitchen odour

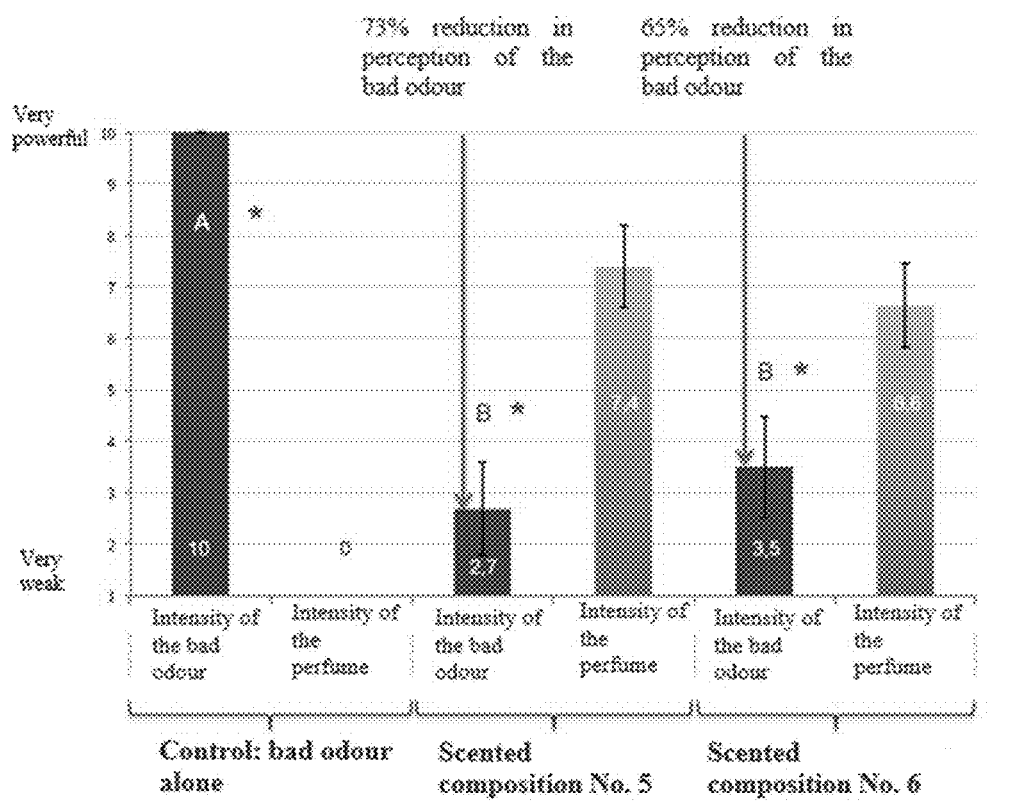
Figure 3 : Results of the sensory evaluation against the bad toilet odour

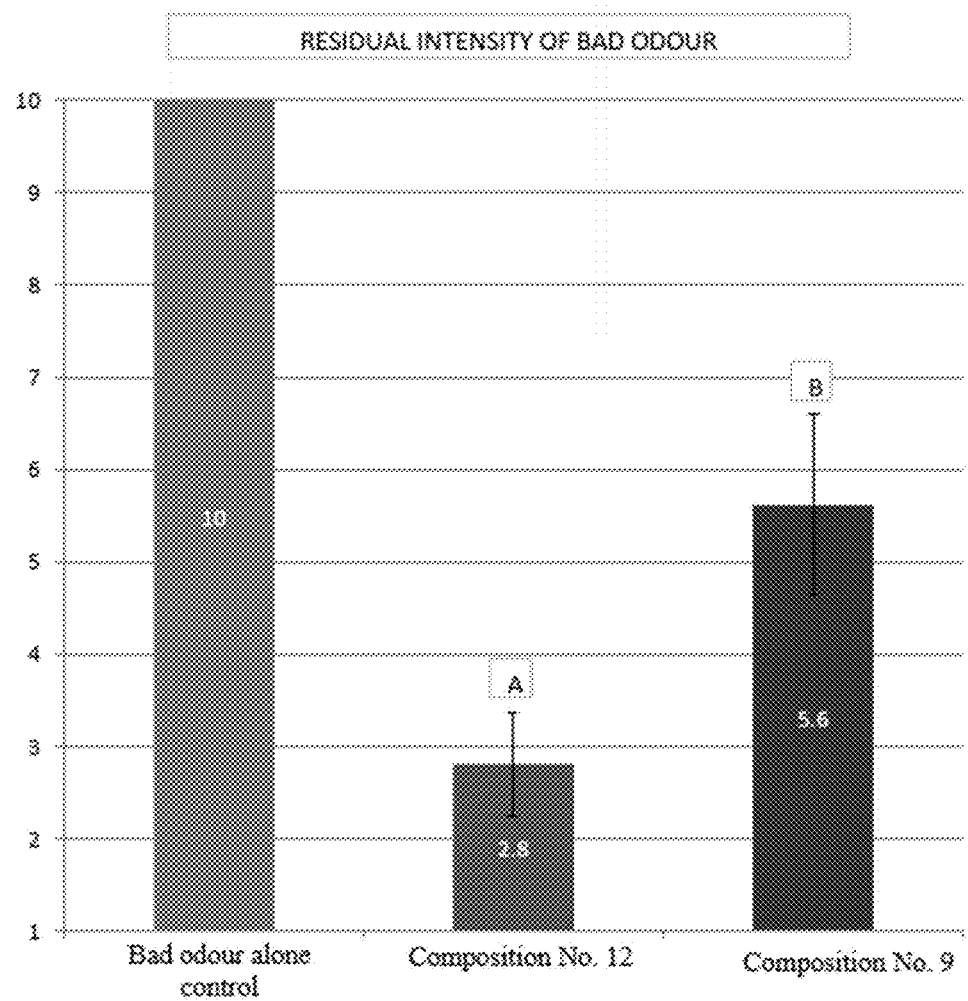
Figure 4 : Comparison of the scented compositions No. 12 and No. 9

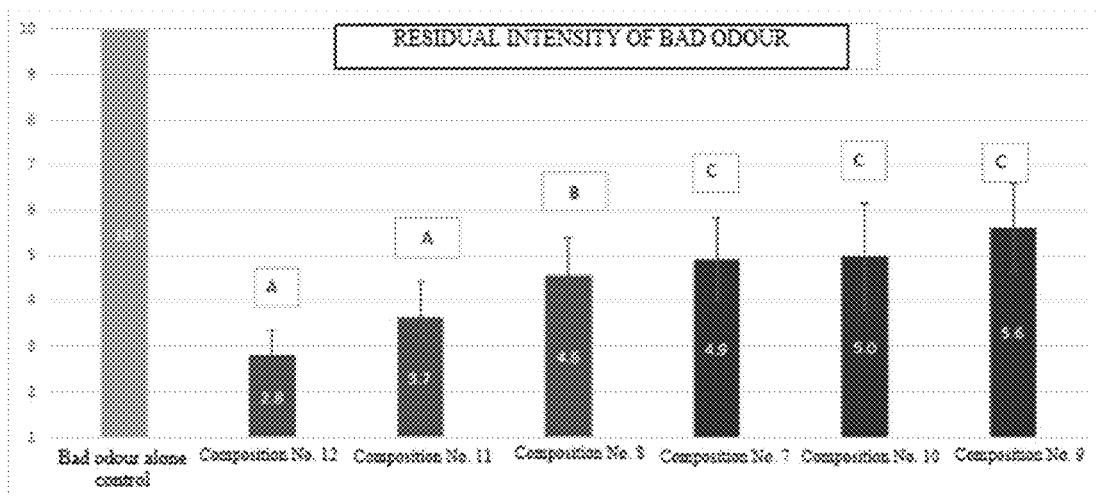
Figure 5 : Residual intensity of bad toilet odour of the tested compositions No. 12, No. 11, No. 8, No. 7, No. 10 and No. 9 in comparison to the bad odour alone control
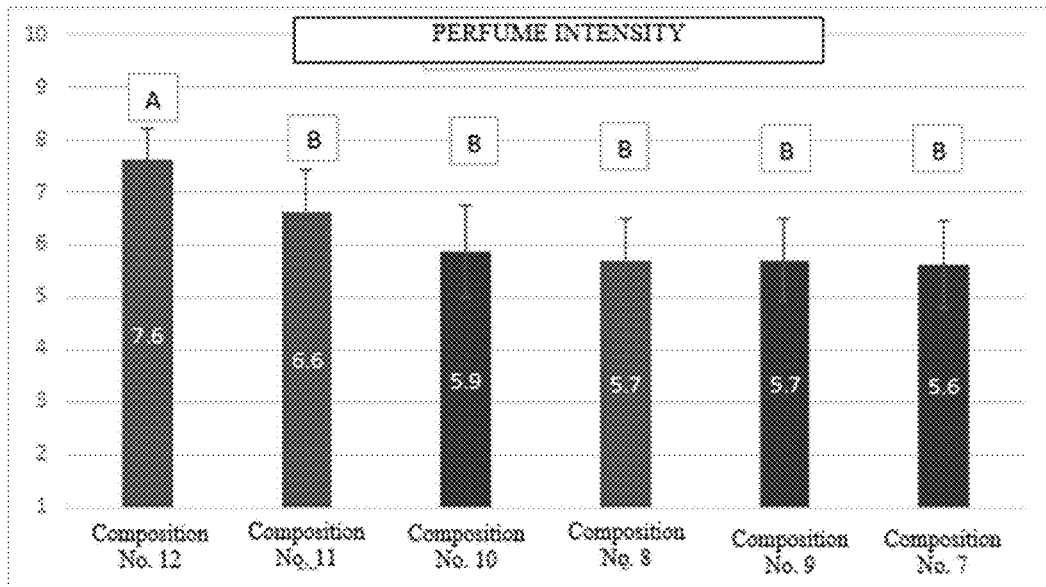
Figure 6 : Intensity of the perfume of the tested compositions No. 12, No. 11, No. 10, No. 8, No. 9 and No.7

MIXTURE COMPRISING AT LEAST DIHYDRO-5-PENTYL-2(3H)-FURANONE AND 2,4-DIMETHYL-4-PHENYLTETRAHYDROFURAN AND USE THEREOF FOR MASKING UNPLEASANT ODOURS

The object of the present invention is a mixture comprising at least dihydro-5-pentyl-2(3H)-furanone and 2,4-dimethyl-4-phenyltetrahydrofuran, and its use to mask bad odours.

In humans, the olfactory system consists of a set of sensors. An odour is perceptible when it reaches a threshold of olfactory perception. The threshold of olfactory perception corresponds to a concentration of odoriferous molecules per litre of air. One can also refer to a threshold of discernment reached when an individual is capable of differentiating, discriminating, judging and evaluating an odour. Thus, in a sample, the concentration of the odoriferous molecules plays an important role for the perception of odours.

During olfaction, the odoriferous molecules move up the nasal cavity to reach the olfactory epithelium in which the olfactory nerve cells are located. The odoriferous molecules are captured by the olfactory nerve cells in order to cause a cascade of reactions leading to the formation of a nerve message. In the central nervous system, the olfactory bulb receives the nerve messages and allows their transport to the olfactory cortex in which they are identified and associated with olfactory values.

Olfactory perception allows to characterise the odours by their intensity, their quality and their evaluation. The intensity of an odour is defined by the quantity of odoriferous molecules. The quality of the odours is related to the identity of the odoriferous molecule. The evaluation of an odour refers to the pleasant or unpleasant nature of an olfactory sensation.

The mixtures of odoriferous molecules, both of natural origin and synthetic, can be used in cosmetics, in perfumery, or for cleaning products. These mixtures allow to provide a pleasant olfactory component to the user. For certain uses, this pleasant olfactory component can be disturbed by other unpleasant olfactory components such as the active principles of the product containing said odoriferous mixture or by an outside factor (odour of tobacco, body odour etc.).

The olfactory component regarded as pleasant must therefore be sufficiently intense to compensate for the olfactory component regarded as unpleasant. Finding the balance between the pleasant and unpleasant olfactory components is therefore a major problem in the perfume industry.

Moreover, for any later use, the odoriferous mixtures must be stable, that is to say, not degrade over time and not react with the other components of the product that contains them.

In perfumery, obtaining an odoriferous mixture that is polyvalent in terms of uses, that is stable, pleasant and allows to mask bad odours, is the subject of constant research.

The inventors have developed a mixture comprising at least dihydro-5-pentyl-2(3H)-furanone and 2,4-dimethyl-4-phenyltetrahydrofuran. The object of the present invention allows to obtain an odoriferous mixture with improved intensity and longevity, capable of masking bad odours, wherein said mixture can be integrated into any type of perfume, i.e. into any olfactory family.

The object of the present invention is therefore a mixture comprising, preferably consisting of, dihydro-5-pentyl-2(3H)-furanone (gamma-nonalactone) at a percentage between 20 and 80% relative to the total weight of said mixture and 2,4-dimethyl-4-phenyltetrahydrofuran (rhubafuran) at a percentage between 20 and 80% relative to the total weight of said mixture.

BRIEF DESCRIPTION OF THE DRAWINGS

Aspects of the present disclosure are best understood from the following detailed description when read in conjunction with the accompanying figures. It is noted that, in accordance with the standard practice in the industry, various features are not drawn to scale. In fact, the dimensions of the various features may be arbitrarily increased or reduced for clarity of discussion.

FIG. 1 is a bar chart showing the results of a sensory evaluation of the performance of embodiments of the scented products against unpleasant tobacco odours.

FIG. 2 is a bar chart showing the results of a sensory evaluation of the performance of embodiments of the scented products against unpleasant kitchen odours.

FIG. 3 is a bar chart showing the results of a sensory evaluation of the performance of embodiments of the scented products against unpleasant toilet odours.

FIG. 4 is a bar chart showing comparison of the results of sensory evaluations with composition numbers 12 and 9.

FIG. 5 is a bar chart showing comparison of the results of sensory evaluations with composition numbers 12, 11, 10, 9, 8, and 7.

FIG. 6 is a bar chart showing comparison of the results of sensory evaluations with composition numbers 12, 11, 10, 9, 8, and 7.

The object of the present invention is also a mixture comprising, preferably consisting of, dihydro-5-pentyl-2(3H)-furanone at a percentage between 20 and 75% relative to the total weight of said mixture and 2,4-dimethyl-4-phenyltetrahydrofuran at a percentage between 20 and 75% relative to the total weight of said mixture.

According to the invention, "mixture", "masking mixture" or "odoriferous mixture" means a mixture comprising at least dihydro-5-pentyl-2(3H)-furanone and 2,4-dimethyl-4-phenyltetrahydrofuran. The mixture according to the present invention can further comprise ethyl ester of 10-undecenoic acid (ethyl undecylenate) and/or (3E)-4-(2,6,6-trimethylcyclohex-2-en-1-yl)but-3-en-2-one (alpha-ionone). In the sense of the present invention, "mixture", "masking mixture" and "odoriferous mixture" will be used indifferently.

Dihydro-5-pentyl-2(3H)-furanone and 2,4-dimethyl-4-phenyltetrahydrofuran can be used in proportions that vary according to the desired use.

Preferably, the dihydro-5-pentyl-2(3H)-furanone represents, in the mixture according to the invention, between 30 and 35% relative to the total weight of said mixture and the 2,4-dimethyl-4-phenyltetrahydrofuran represents, in the mixture according to the invention, between 30 and 35% relative to the total weight of said mixture.

In a preferred embodiment, the mixture according to the invention further comprises ethyl ester of 10-undecenoic acid and/or (3E)-4-(2,6,6-trimethylcyclohex-2-en-1-yl)but-3-en-2-one.

In a specific embodiment, said mixture consists of dihydro-5-pentyl-2(3H)-furanone, 2,4-dimethyl-4-phenyltetrahydrofuran, ethyl ester of 10-undecenoic acid and/or (3E)-4-(2,6,6-trimethylcyclohex-2-en-1-yl)but-3-en-2-one.

The ethyl ester of 10-undecenoic acid and the (3E)-4-(2,6,6-trimethylcyclohex-2-en-1-yl)but-3-en-2-one can be used in proportions that vary according to the desired use.

Preferably, the concentration of ethyl ester of 10-undecenoic acid in the mixture according to the invention is between 20 and 75% relative to the total weight of said mixture and the concentration of the (3E)-4-(2,6,6-trimethylcyclohex-2-en-1-yl)but-3-en-2-one in the mixture according to the invention is between 20 and 75% relative to the total weight of said mixture.

Even more preferably, the concentration of ethyl ester of 10-undecenoic acid in the mixture according to the invention is between 30 and 35% relative to the total weight of said mixture and the concentration of the (3E)-4-(2,6,6-trimethylcyclohex-2-en-1-yl)but-3-en-2-one in the mixture according to the invention is between 30 and 35% relative to the total weight of said mixture.

In a specific embodiment, the mixture according to the invention comprises 35% dihydro-5-pentyl-2(3H)-furanone relative to the total weight of said mixture, 35% 2,4-dimethyl-4-phenyltetrahydrofuran relative to the total weight of said mixture, and 30% ethyl ester of 10-undecenoic acid relative to the total weight of said mixture.

In another specific embodiment, the mixture according to the invention comprises 50% dihydro-5-pentyl-2(3H)-furanone relative to the total weight of said mixture and 50% 2,4-dimethyl-4-phenyltetrahydrofuran relative to the total weight of said mixture.

In another specific embodiment, the mixture according to the invention comprises 75% dihydro-5-pentyl-2(3H)-furanone relative to the total weight of said mixture and 25% 2,4-dimethyl-4-phenyltetrahydrofuran relative to the total weight of said mixture.

In another specific embodiment, the mixture according to the invention comprises 35% dihydro-5-pentyl-2(3H)-furanone relative to the total weight of said mixture, 35% 2,4-dimethyl-4-phenyltetrahydrofuran relative to the total weight of said mixture, and 30% (3E)-4-(2,6,6-trimethylcyclohex-2-en-1-yl)but-3-en-2-one relative to the total weight of said mixture.

In another specific embodiment, the mixture according to the invention comprises 60% dihydro-5-pentyl-2(3H)-furanone relative to the total weight of said mixture, 20% 2,4-dimethyl-4-phenyltetrahydrofuran relative to the total weight of said mixture, and 20% (3E)-4-(2,6,6-trimethylcyclohex-2-en-1-yl)but-3-en-2-one relative to the total weight of said mixture.

In another specific embodiment, the mixture according to the invention comprises 30% dihydro-5-pentyl-2(3H)-furanone relative to the total weight of said mixture, 30% 2,4-dimethyl-4-phenyltetrahydrofuran relative to the total weight of said mixture, 20% ethyl ester of 10-undecenoic acid relative to the total weight of said mixture, and 20% (3E)-4-(2,6,6-trimethylcyclohex-2-en-1-yl)but-3-en-2-one relative to the total weight of said mixture.

The object of the present invention is also a composition that comprises the mixture according to the invention.

Thus, "composition" means a composition comprising the mixture according to the invention. Typically, this composition is a scented composition.

Preferably, the composition according to the invention comprises between 0.5 and 50%, preferably between 0.5 and 5% of mixture according to the invention, relative to the total weight of said composition.

The object of the present invention is therefore a composition comprising dihydro-5-pentyl-2(3H)-furanone at a percentage between 0.1 and 15%, preferably between 0.1 and 10%, preferably between 0.1 and 3.75% relative to the total weight of said composition and 2,4-dimethyl-4-phenyltetrahydrofuran at a percentage between 0.1 and 15%, preferably between 0.1 and 10%, preferably between 0.1 and 3.75% relative to the total weight of said composition.

The dihydro-5-pentyl-2(3H)-furanone can be used in proportions that vary according to the desired use.

Preferably, the dihydro-5-pentyl-2(3H)-furanone is present in the composition according to the invention at a concentration between 0.1 and 15%, preferably between 0.1 and 3.75%, preferably between 0.1 and 0.75%, more preferably between 0.2 and 0.75% and even more preferably between 0.2 and 0.375% relative to the total weight of said composition.

The 2,4-dimethyl-4-phenyltetrahydrofuran can be used in proportions that vary according to the desired use.

Preferably, the 2,4-dimethyl-4-phenyltetrahydrofuran is present in the composition according to the invention at a concentration between 0.1 and 15%, preferably between 0.1 and 3.75%, preferably between 0.1 and 0.75%, more preferably between 0.2 and 0.75% and even more preferably between 0.2 and 0.375% relative to the total weight of said composition.

In a specific embodiment, the composition according to the invention further comprises ethyl ester of 10-undecenoic acid and/or (3E)-4-(2,6,6-trimethylcyclohex-2-en-1-yl)but-3-en-2-one.

The ethyl ester of 10-undecenoic acid can be used in proportions that vary according to the desired use.

Preferably, the ethyl ester of 10-undecenoic acid is present in the composition according to the invention at a concentration between 0.1 and 3.75%, preferably between 0.1 and 0.75%, more preferably between 0.2 and 0.75% and even more preferably between 0.2 and 0.375% relative to the total weight of said composition.

The (3E)-4-(2,6,6-trimethylcyclohex-2-en-1-yl)but-3-en-2-one can be used in proportions that vary according to the desired use.

Preferably, the (3E)-4-(2,6,6-trimethylcyclohex-2-en-1-yl)but-3-en-2-one is present in the composition according to the invention at a concentration between 0.1 and 3.75%, preferably between 0.1 and 0.75%, more preferably between 0.2 and 0.75% and even more preferably between 0.2 and 0.375% relative to the total weight of said composition.

In a specific embodiment, the composition according to the invention comprises between 0.35 and 5.5% dihydro-5-pentyl-2(3H)-furanone relative to the total weight of said composition, 0.35% 2,4-dimethyl-4-phenyltetrahydrofuran relative to the total weight of said composition and 0.30% ethyl ester of 10-undecenoic acid relative to the total weight of said composition.

In another specific embodiment, the composition according to the invention comprises 0.50% dihydro-5-pentyl-2(3H)-furanone relative to the total weight of said composition and 0.50% 2,4-dimethyl-4-phenyltetrahydrofuran relative to the total weight of said composition.

In another specific embodiment, the composition according to the invention comprises 0.75% dihydro-5-pentyl-2(3H)-furanone relative to the total weight of said composition and 0.25% 2,4-dimethyl-4-phenyltetrahydrofuran relative to the total weight of said composition.

In another specific embodiment, the composition according to the invention comprises between 0.35 and 0.45% dihydro-5-pentyl-2(3H)-furanone relative to the total weight of said composition, 0.35% 2,4-dimethyl-4-phenyltetrahydrofuran relative to the total weight of said composition, and 0.30% (3E)-4-(2,6,6-trimethylcyclohex-2-en-1-yl)but-3-en-2-one relative to the total weight of said composition.

In another specific embodiment, the composition according to the invention comprises 0.60% dihydro-5-pentyl-2

(3H)-furanone relative to the total weight of said composition, 0.20% 2,4-dimethyl-4-phenyltetrahydrofuran relative to the total weight of said composition, and 0.20% (3E)-4-(2,6,6-trimethylcyclohex-2-en-1-yl)but-3-en-2-one relative to the total weight of said composition.

In another specific embodiment, the composition according to the invention comprises 0.30% dihydro-5-pentyl-2 (3H)-furanone relative to the total weight of said composition, 0.30% 2,4-dimethyl-4-phenyltetrahydrofuran relative to the total weight of said composition, 0.20% ethyl ester of 10-undecenoic acid relative to the total weight of said composition, and 0.20% (3E)-4-(2,6,6-trimethylcyclohex-2-en-1-yl)but-3-en-2-one relative to the total weight of said composition.

In a specific embodiment, the composition according to the invention is a scented composition.

"Scented composition" means a composition comprising a mixture of perfuming substances, both in the isolated state and in solution or in suspension, in their usual diluents, solvents or co-ingredients. Such a composition is intended to provide a pleasant olfactory component.

Such a scented composition can comprise esters, ethers, alcohols, aldehydes, ketones, lactones, acetals, nitriles, phenols, acids, terpenes, saturated or unsaturated nitrogen or sulphur heterocyclic compounds, and products of natural origin.

Examples of esters include, but are not limited to, benzyl acetate, p-tert-butylcyclohexyl acetate, linalyl acetate, dimethyl-benzyl-carbinyl acetate, phenylethyl acetate, 1,1-dimethyl-2-phenylethyl acetate, linalyl benzoate, ethyl-methyl-phenyl glycinate, allylcyclohexyl propionate, styrallyl propionate, benzyl salicylate, methyl-3-oxo-2-pentylcyclopentane acetate, prop-2-enyl-2,3-methylbutoxy acetate (allyl amyl glycolate, 2-propenyl ester of 3-methylbutoxy-acetic acid), phenylmethyl ester of acetic acid, isoamyl acetate (isopentyl acetate), cis-hex-3-enyl acetate ((Z)-hex-3-enyl acetate), citronellyl acetate (3,7-dimethyl-6-octen-1-ol acetate), hexyl acetate, isobornyl acetate (bicyclo[2.2.1]heptan-2-ol,1,7,7-trimethyl exo-acetate), methanyl acetate (alpha,alpha,4-trimethylcyclohexylmethyl acetate), ethyl acetate, prenyl acetate (3-methyl-2-butenyl acetate), terpenyl acetate (4-methyl-1-propan-2-yl-1-cyclohex-2-enyl acetate), alpha-3,3-trimethylcyclohexyl-methyl formate, 3-methylbutyl butanoate (iso amyl butyrate), alpha,alpha-dimethylphenethyl butanoate, 3-dihydrodicyclopentadien-2,3-yl acetate, prop-2-enyl, 3-cyclohexyl propanoate (allyl cyclo hexane propionate), allyl heptanoate (2-propenyl heptanoate), 2-phenoxy-ethyl 2-methylpropanoate (phenoxy ethyl isobutyrate), ethyl 2-methyl-pentanoate, ethyl 2-methyl-butyrate (ethyl ester of 2-methyl-butanoic acid), 1,4-dioxacycloheptadecane-5,17-dione (ethylene Brassylate), (2S)-2-propyl-1,1-dimethyl-propoxy propanoate ((2S)-propyl Ester of 2-(1,1-dimethylpropoxy)-propanoic acid), 2-tert-butylcyclohexyl acetate (2-(1,1-dimethylethyl) cyclohexyl acetate), ci-3-hexenyl salicylate, [(1S)-3-(4-methylpent-3-enyl)-1-cyclohex-3-enyl]methyl acetate, 3-pentyltetrahydro[2H]pyranyl acetate, linalyl propionate, cedryl acetate, anisyl acetate, nopyl acetate, neryl acetate, 3a,4,5,6,7,7a-hexahydro-4,7-methanoinden-6-yl acetate, 3a,4,5,6,7,7a-hexahydro-4,7-methano-1H-inden-6-yl propanoate, 2-propenyl 3-cyclohexanepropanoate, 1,2,3-triethyl 2-hydroxypropane-1,2,3-tricarboxylate, (2E)-3,7-dimethylocta-2,6-dien-1-yl acetate, 3,5,5-trimethylhexyl acetate, 3,7-dimethyl-octa-1,6-dien-3-yl acetate, cis-3,7-dimethyl-2,6-octadienyl ethanoate, 1-methylethyl ester of tetradecanoic acid, 3-methylbutyl ester of 2-hydroxy-benzoic acid, phenylmethyl ester of 2-hydroxy-benzoic acid, 2-hexyl ester of 2-hydroxy-benzoic acid, methyl ester of 2-hydroxy-Benzoic acid, ethyl ester of acetoacetic acid, 3,7-dimethyl-octa-1,6-dien-3-yl acetate, 1,2-diethyl ester of 1,2-benzenedicarboxylic acid, (Z)-hex-3-enyl 2-methylpropanoate, (4-methyl-1-propan-2-yl-1-cyclohex-2-enyl) acetate, 3a,4,5,6,7,7a-hexahydro-4,7-methanoinden-6-yl acetate, ethyl 2,3-epoxy-3-phenylbutyrate, methyl 2-aminobenzoate, methyl 2-(methylamino)benzoate, methyl benzoate, methyl 2,4-dihydroxy-3,6-dimethylbenzoate, (3R-(3alpha,3beta,6beta,7beta,8alpha))-octahydro-6-methoxy-3,6,8,8-tetramethyl-1H-3a,7-methanoazulene acetate and hexyl salicylate. Preferably, examples of esters include, but are not limited to, linalyl propionate, cedryl acetate, anisyl acetate, nopyl acetate, neryl acetate, (3R-(3alpha,3beta,6beta,7beta,8alpha))-octahydro-6-methoxy-3,6,8,8-tetramethyl-1H-3a,7-methanoazulene acetate and hexyl salicylate.

Examples of ethers include, but are not limited to, benzyl ether, ethyl ether, ambergris, diphenyl oxide, 4,6,6,7,8,8-hexamethyl-1,3,4,6,7,8-hexahydrocyclopenta[g]isochromene, amber carane, 1,1-dimethoxy-2,2,5-trimethyl-4-hexene, (ethoxymethoxy)cyclododecane, (E)-1-methoxy-4-(1-propenyl)-benzene, 1-methoxy-4-(2-propenyl)-benzene and 2-naphthyl ethyl ether. Preferably, examples of ethers include, but are not limited to, 1,1-dimethoxy-2,2,5-trimethyl-4-hexene and 2-naphthyl ethyl ether.

Examples of alcohols include, but are not limited to, menthol ([1R-(1alpha,2beta,5alpha)]-5-methyl-2-isopropyl-cyclohexanol), citronellol, geraniol, linalool (for example ethyl linalool and tetrahydro linalool), phenylethyl alcohol, terpineol, 2,6-dimethylheptan-2-ol, 2-methyl-1-phenylpropan-2-ol (dimethyl phenyl carbinol), 3-methyl-5-[2,2,3-trimethylcyclopent-3-en-1-yl]pent-4-en-2-ol, 2-phenylethanol, 2-ethyl-4-(2,2,3-trimethyl-1-cyclopent-3-enyl)but-2-en-1-ol, (E)-4-methyldec-3-en-5-ol, cinnamic alcohol (3-phenyl-2-propen-1-ol), 2,6-dimethyloct-7-en-2-ol, alpha,beta,2,2,3-pentamethylcyclopent-3-ene-1-butanol, 3-(5,5,6-trimethylbicyclo[2.2.1]hept-2-yl) cyclohexan-1-ol (IBCH), cis-3-hexen-1-ol, methyl-trimethylbicyclo-hexylmethyl-cyclopropyl methanol benzyl alcohol, endo-1,7,7-trimethyl-bicyclo-[2.2.1]heptan-2-ol, 3,7-dimethyl-6-octen-1-ol, 3,7-dimethyl-1-octanol, (2E)-3,7-dimethyl-2,6-octadien-1-ol, cis-3,7-dimethyl-2,6-octadien-1-ol, 3,7-dimethyl-octa-1,6-diene-3-ol, 2-(4-methyl-1-cyclohex-3-enyl)propan-2-ol, 4-methyl-1-(1-methylethyl)-3-cyclohexen-1-ol, (1R, 2S, 5R)-5-methyl-2-(1-methylethyl)-cyclohexanol, (2E)-3,7-dimethyl-2,6-octadien-1-ol and 3-methylbutan-1-ol. Preferably, examples of alcohols include, but are not limited to, alpha,beta,2,2,3-pentamethylcyclopent-3-ene-1-butanol, 3-(5,5,6-trimethylbicyclo[2.2.1]hept-2-yl) cyclohexan-1-ol (IBCH), cis-3-hexenol, methyl-trimethylbicyclo-hexylmethyl-cyclopropyl methanol, 3-methylbutan-1-ol, ethyl linalool, tetrahydro linalool and [1R-(1 alpha,2beta,5alpha)]-5-meethyl-2-isopropylcyclohexanol (menthol).

Examples of aldehydes include, but are not limited to, the linear alkanals comprising between 8 and 18 atoms of carbons, citral, citronellal, Cyclamen aldehyde, hydroxycitronellal, 3-(4-tert-butylphenyl)-2-methylpropanal, 3-(4-tert-butylphenyl)propanal, 2,6,10-trimethylundec-9-enal, 4(octahydro-4,7-methano[5H]inden-5-ylidene)butanal, 3-(3-propan-2-ylphenyl)butanal, 7-hydroxy-3,7-dimethyl-octanal (hydroxycitronellal, 3,7-dimethyl-7-hydroxy-octane-1-al), 4-(4-hydroxy-4-methylpentyl)cyclohex-3-ene-1-carbaldehyde, octahydro-5-methoxy-4,7-methano-1H-indene-2-carboxaldehyde, alpha-methyl cinnamic aldehyde (2-methyl-3-phenyl-2-propenal), 4-methoxybenzaldehyde (anisic Aldehyde), C10 aldehyde (decanal), undec-10-enal, C12 aldehyde (lauric or dodecanal), methyl-nonyl acetaldehyde (2-methylundecanal), C16 aldehyde, C6 aldehyde (hexanal), cinnamic aldehyde (3-phenyl-2-propenal), 3-ethyoxy-4-hydroxybenzaldehyde (Ethylvanillin), hexyl cinnamic aldehyde (2-benzylideneheptanal), 3-phenylbutanal (3-phenylbutyraldehyde), 2,4-dimethylcyclohex-3-ene-1-carbaldehyde, 5-heptanal, 2,6-dimethylhept-5-enal, 4-hydroxy-3-methoxybenzaldehyde (Vanillin), alpha-methyl-1,3-benzodioxole-5-propionaldehyde, 4-isopropylbenzaldehyde, 3,7-dimethyl-6-octenal, 3,7-dimethyl-2,6-octadienal, 4-(4-hydroxy-4-methylpentyl)-3-cyclohexene-1-carboxaldehyde, trans-hex-2-enal, 2,4,6-trimethyl-3-cyclohexene-1-carboxaldehyde, 2-(4-tert-butylbenzyl)propionaldehyde and benzaldehyde. Preferably, examples of aldehydes include, but are not limited to, 2,4-dimethylcyclohex-3-ene-1-carbaldehyde, 5-heptanal, 2,6-dimethyl-hept-5-enal, 4-hydroxy-3-methoxybenzaldehyde (Vanillin), alpha-methyl-1,3-benzodioxole-5-propionaldehyde and benzaldehyde.

Examples of ketones include, but are not limited to, the ionones, isomethylionone, methyl cedryl, (E)-1-(2,6,6-trimethyl-1-cyclohex-2-enyl)but-2-en-1-one (alpha-damascone), 3-methyl-2-[(2Z)-pent-2-en-1-yl]cyclopent-2-en-1-one (cis-jasmone), 4-(4-methoxyphenyl)-butan-2-one, 4(3)-(4-methylpent-3-enyl)cyclohex-3-enecarbaldehyde, methyl cedryl ketone, 7-methylbenzo[b][1,4]dioxepin-3-one, 1,7,7-trimethylbicyclo[2,2,1]heptan-2-one, 1-benzopyrane-2-one (Coumarin), 1-(2,6,6-trimethyl-1-cyclohex-3-enyl)but-2-en-1-one, butan-2,3-dione (Diacetyl), 1-(1,2,3,4,5,6,7,8-octahydro-2,3,8,8,-tetramethyl-2-naphthyl)ethan-1-one, irones, 1-(2-naphthalenyl)ethanone (2-acetonaphthone), menthone, carvone, 3-methyl-2-pentyl-2-cyclopentenone, 1-(2,6,6-trimethyl-3-cyclohexen-1-yl)-2-buten-1-one, 1-(2,6,6-trimethyl-2-cyclohexenyl)hepta-1,6-dien-3-one, 2-ethyl-3-hydroxy-4H-pyran-4-one, (5R)-2-methyl-5-prop-1-en-2-ylcyclohex-2-en-1-one, 1-(6-tert-butyl-1,1-dimethyl-2,3-dihydro-1H-inden-4-yl)ethanone, 1-(5,6,7,8-tetrahydro-3,5,5,6,8,8-hexamethyl-2-naphthyl)ethan-1-one, 4-(2,6,6-trimethylcyclohex-2-enyl)-but-3-ene-2-one, octan-2-one and 1,3,4,6,7,8a-Hexahydro-1,1,5,5-tetramethyl-2H-2,4a-methanonaphthalen-8(5H)-one. Preferably, examples of ketones include, but are not limited to, the irones, 1-(2-naphthalenyl)ethanone (2-acetonaphthone), menthone, carvone, 3-methyl-2-pentyl-2-cyclopentenoneand 1,3,4,6,7,8a-Hexahydro-1,1,5,5-tetramethyl-2H-2,4a-methanonaphthalen-8(5H)-one.

Examples of lactones include, but are not limited to, gamma decalactone (decan-4-olide), gamma undecalactone (undecan-4-olide), cis-jasmone lactone, gamma undecalactone, delta octalacone, delta decalactone and hexahydro-3,6-dimethyl-2(3H)-benzofuranone. Preferably, examples of lactones include, but are not limited to, gamma undecalactone, delta octalacone, delta decalactone and hexahydro-3,6-dimethyl-2(3H)-benzofuranone.

Examples of acetals include, but are not limited to, 2,4-dimethyl tetrahydroindenodioxine, diacetal of phenylacetic aldehyde, phenylacetaldehyde glycerylacetal, citral diethyl acetal, citral dimethyl acetal, 2,6-octadienal, 1,1-dimethoxy-2-phenylethane and isomerised 3,7-dimethyl acid. Preferably, examples of acetals include, but are not limited to, phenylacetaldehyde glycerylacetal, citral diethyl acetal, citral dimethyl acetal, 2,6-octadienal, and isomerised 3,7-dimethyl acid.

Examples of nitriles include, but are not limited to, 3,7-dimethyloct-6-ene nitrile (citronellyl nitrile), tridec-2-enenitrile, 3-phenyl-2-propenenitrile, dodecanenitrile and 3,7-dimethylnona-2,6-dienenitrile. Preferably, examples of nitriles include, but are not limited to, tridec-2-enenitrile, 3-phenyl-2-propenenitrile, dodecanenitrile and 3,7-dimethylnona-2,6-dienenitrile.

Examples of phenols include, but are not limited to, eugenol (2-methoxy-4-(2-propenyl)-phenol), iso-eugenol, 5-methyl-2-(1-methylethyl)-phenol, 2-ethoxy-4-methylphenol, 2,6-di-tert-butyl-p-cresol and 2-ethoxy-4-(methoxymethyl)-phenol.

Examples of acids include, but are not limited to, pentanoic acid, butyric acid and 2-methylpent-2-en-1-oic acid.

Examples of terpenes such as cyclic (for example sesquiterpenic) or non-cyclic terpene hydrocarbons include, but are not limited to, limonene, 1-methyl-4-isopropenyl-1-cyclohexene, 1-methyl-4-isopropyl-1,4-cyclohexadiene, 7-methyl-3-methyleneocta-1,6-diene, 1-methyl-4-(1-methylethyl)-1,3-cyclohexadiene, 2,6,6-trimethylbicyclo[3.1.1]hept-2-ene, 6,6-dimethyl-2-methylenebicyclo[3.1.1]heptane, 2,2-dimethyl-3-methylenebicyclo-[2.2.1]-heptane, [1R,(1R*,4E,9S*)]-4,11,11-trimethyl-8-methylene-bicyclo [7.2.0]undec-4-ene, 1-methyl-4-(1-methylethyl)benzene and the essential oils containing sesquiterpenes. Preferably, examples of terpenes include, but are not limited to, essential oils containing sesquiterpenes.

Examples of saturated or unsaturated nitrogen or sulphur heterocyclic compounds include, but are not limited to, indole, 1,3-benzopyrrole, tetrahydro-4-methyl-2-(2-methyl-1-propenyl)-2H-pyrane, 2-methyl-pyrazine, 4-methyl-5-hydroxyethyl thiazole (2-(4-methylthiazol-5-yl)ethanol), 6-tert-butylquinoline, 6-(isopropyl)quinoline, cis-2-methyl-4-propyl-1,3-oxathianeand the pyrazines. Preferably, examples of saturated or unsaturated nitrogen or sulphur heterocyclic compounds include, but are not limited to, 6-tert-butylquinoline, 6-(isopropyl)quinoline, cis-2-methyl-4-propyl-1,3-oxathiane and the pyrazines.

Examples of products of natural origin include, but are not limited to, essential oils extracted from the various plant parts (flowers, stems, leaves, fruit, bark, roots, woody parts, grasses, needles, sap and gums), resinoids, concretes, or absolutes obtained from the latter. Preferably, examples of products of natural origin include, but are not limited to, white wormwood oil (*Artemisia Herba-Alba*), extract of lemon tree bark (Citrus Limon Peel extract), *Eucalyptus globulus* leaf oil, *Dipterocarpus turbinatus* oil (*Dipterocarpus turbinatus* Balsam Oil), *Pogostemon cablin* leaf oil, *Rosmarinus officinalis* leaf oil, *Juniperus virginiana* oil, field mint leaf oil (*Mentha Arvensis*), spearmint leaf oil (*Mentha viridis*), *Citrus Aurantium Dulcis* bark oil, extract of bark of *Citrus Aurantium Dulcis*, Mediterranean cypress leaf oil (*Cupressus sempervirens*), Patchouli leaf oil (*Pogostemon cablin*), Texas Cedar oil (*Juniperus Mexicana*) and the oil of Hybrid Lavandula (*Lavandula Hybrida*).

The scented composition can comprise ingredients of natural or synthetic origin. The choice of this scented composition depends on the one hand on the desired odoriferous effect and on the other hand on the nature of the product that contains it.

The scented composition according to the invention is intended to be applied or sprayed onto a surface or into the air in order to confer a pleasant odour.

"Pleasant odour" means an odour that is detected by the olfactory sense of humans and that is perceived as pleasant.

The scented composition according to the invention can further comprise bactericidal agents, bacteriostatic agents, insecticides and repulsive agents.

The object of the present invention is also a cosmetic base comprising the mixture or the scented composition of the present invention.

"Cosmetic base" means a cosmetic product or a product for hygienic care in the form of a cream, an emulsion, a foam, a wax, an oil, a lotion, a gel, a suspension, a solution, a powder, a balm, a serum, a mask or a scrub. Examples of cosmetic products, include, but are not limited to, perfumes, eaux de parfums, eaux de toilette, hair products, shaving and after-shave products, essential oils, treatments for the skin, deodorants, antiperspirants, depilatory products, self-tanning products, sun protection, make-up products, etc. Examples of hygienic care include, but are not limited to, wipes, talcs, diapers, bibs, tissues, paper towels, soaps, showers gel, shampoos and other products for washing the body, mouth and dental care, feminine hygiene products, etc.

Such products can be both intended for humans and animals.

The object of the present invention is also a detergent base comprising the mixture or the scented composition of the present invention.

"Detergent base" means products for maintenance or cleaning. Examples of products for maintenance or cleaning include, but are not limited to, detergents for surfaces, for textiles and for dishes, bleaching agents, softening agents, fabric softeners, stripping agents, varnishes and other household cleaning products.

The object of the present invention is also herbicidal products and fertilisers comprising the mixture or the scented composition of the present invention.

The object of the present invention is also a home fragrance comprising the mixture or the scented composition of the present invention.

"Home fragrance" means products intended to perfume the air. "Home fragrances" can, in a non-limiting way, be contained in aerosol, sprayers, sprays, candles, scented gels, solid substrates, perfume burners, incense, balls and diffusers of perfumes. The home fragrance of the present invention can be used for public, professional or private enclosed spaces; for example, a car, house, administrative buildings, public transportation, museums, historical monuments, churches, basements, schools, restaurants, cinemas, hospitals, factories, water or waste treatment plants, boutiques and hotels. The home fragrance can also be used in air conditioning systems.

The present invention also relates to materials comprising or coated with the mixture or with the scented composition according to the invention, in particular polymers such as for example plastics, macromolecules such as for example cellulose, etc.

The mixture or the scented composition according to the invention are intended to be applied in concentrated or non-concentrated form in cosmetic bases, detergent bases or home fragrances.

The object of the present invention is also the use of the mixture according to the invention to prepare a cosmetic composition, a detergent base or a home fragrance.

The object of the present invention is also the use of the mixture, of the scented composition according to the invention, of the cosmetic base, of the detergent base or of the home fragrance in order to mask bad odours.

"Bad odours" means odours which are detected by the olfactory sense of humans and which are perceived as offensive or unpleasant. In the sense of the present invention, the bad odours to be masked can result intrinsically from the cosmetic base, detergent or the home fragrance itself, or come from the outside environment.

"Mask bad odours" means the modification of the qualitative perception of the odour via the addition of a substance or of a mixture of substance capable of providing a new, distinct and pleasant odour.

In a specific embodiment, the mixture or the scented composition of the present invention mask bad odours without degrading the molecules responsible for the bad odours. Indeed, the molecules of the mixture masking the scented composition mask in an olfactory manner the molecules responsible for the bad odours.

The present invention will be described in more detail using the following examples which are purely for informational purposes.

EXAMPLES

Example 1: Scented Composition No. 1

The masking mixture and the other components of scented composition No. 1, described in table 1, are mixed in order to obtain the scented composition.

TABLE 1

| Designation of the product | % By weight Quantity |
|---|---|
| 2-propenyl ester of 3-methylbutoxy-acetic acid | 0.027 |
| Isopentyl acetate | 0.667 |
| (Z)-hex-3-enyl acetate | 0.100 |
| 3,7-dimethyl-6-octen-1-ol acetate | 0.033 |
| Hexyl acetate | 0.667 |
| Bicyclo[2.2.1]heptan-2-ol,1,7,7-trimethyl exo-acetate | 0.333 |
| Alpha,alpha,4-trimethylcyclohexylmethyl acetate | 0.533 |
| 3-methyl-2-butenyl acetate | 0.167 |
| 4-methyl-1-propan-2-yl-1-cyclohex-2-enyl acetate | 0.667 |
| 3-phenyl-2-propen-1-ol | 4.000 |
| 2-methyl-3-phenyl-2-propenal | 4.667 |
| p-methoxybenzaldehyde | 1.333 |
| Decanal | 0.067 |
| Dodecanal | 0.047 |
| 2-methylundecanal | 0.067 |
| Ethyl 2,3-epoxy-3-phenylbutyrate | 0.101 |
| Dihydro-5-pentyl-2(3H)-furanone | 4.667 |
| Hexanal | 0.027 |
| 3-phenyl-2-propenal | 0.533 |
| 2-phenylethanol | 0.133 |
| Alpha,3,3-trimethylcyclohexylmethyl formate | 0.500 |
| 3-methylbutyle butanoate | 0.167 |
| 1,7,7-trimethylbicyclo[2.2.1]-2-heptanone | 0.133 |
| 3,7-dimethyloct-6-enenitrile | 0.007 |
| 2H-1-benzopyran-2-one | 1.000 |
| 3a,4,5,6,7,7a-hexahydro-4,7-methanoinden-6-yl acetate | 0.333 |
| 3a,4,5,6,7,7a-hexahydro-4,7-methano-1H-inden-6-yl propanoate | 0.333 |
| 2-propenyl 3-cyclohexanepropanoate | 0.120 |
| 1-(2,6,6-trimethyl-3-cyclohexen-1-yl)-2-buten-1-one | 0.133 |
| 2,6-dimethyloct-7-en-2-ol | 1.333 |
| 2,3-butanedione | 0.007 |
| 1,1'-oxydipropan-2-ol | 47.527 |
| 3-ethoxy-4-hydroxybenzaldehyde | 1.333 |
| 2-methoxy-4-(2-propenyl)-phenol | 0.667 |
| Undecan-4-olide | 0.002 |
| Alpha,alpha-dimethylphenethyl butanoate | 0.073 |
| 1-(2,6,6-trimethyl-2-cyclohexenyl)hepta-1,6-dien-3-one | 0.003 |
| 2-phenoxyethyl 2-methylpropanoate | 6.720 |
| 2-ethyl-3-hydroxy-4H-pyran-4-one | 0.667 |
| 1,2,3-triethyl 2-hydroxypropane-1,2,3-tricarboxylate | 0.200 |
| 2-methyl-pyrazine | <10 ppm |
| Decan-4-olide | 1.333 |
| 2-propényl heptanoate | 0.333 |
| 1-(1,2,3,4,5,6,7,8-octahydro-2,3,5,5-tetramethyl-2-naphthyl)ethan-1-one | 0.200 |
| 2-benzylideneheptanal | 3.000 |
| 2,4-dimethylcyclohex-3-ene-1-carbaldehyde | 0.800 |

TABLE 1-continued

| Designation of the product | % By weight Quantity |
|---|---|
| Ethyl 2-methylpentanoate | 0.067 |
| Ethyl ester of 2-methyl-butanoic acid | 1.333 |
| 1,4-dioxacycloheptadecane-5,17-dione | 1.667 |
| (2S)-propyl Ester of 2-(1,1-dimethylpropoxy)-propanoic acid | 0.133 |
| 2-(4-methylthiazol-5-yl)ethanol | 0.027 |
| 3-phenylbutyraldehyde | 0.007 |
| 4-methyldec-3-en-5-ol | 0.007 |
| 2-(1,1-dimethylethyl)cyclohexyl acetate | 10.000 |
| 2,4-dimethyl-4-phenyltetrahydrofuran | 0.350 |
| ethyl ester of 10-undecenoic acid | 0.300 |
| Dihydro-5-pentyl-2(3H)-furanone | 0.350 |

Example 2: Scented Composition No. 2

The masking mixture and the other components of scented composition No. 2, described in table 2, are mixed in order to obtain the scented composition.

TABLE 2

| Designation of the product | % By weight Quantity |
|---|---|
| 2-propenyl ester of 3-methylbutoxy-acetic acid | 0.444 |
| phenylmethyl ester of acetic acid | 0.889 |
| (3R-(3alpha,3abeta,6alpha,7beta,8aalpha))-octahydro-3,6,8,8-tetramethyl-1H-3a,7-methanoazulen-5-yl acetate | 0.370 |
| (2E)-3,7-dimethylocta-2,6-dien-1-yl acetate | 0.013 |
| Bicyclo[2.2.1]heptan-2-ol,1,7,7-trimethyl exo-acetate | 0.461 |
| 3,5,5-trimethylhexyl acetate | 0.111 |
| 3,7-dimethyl-octa-1,6-diene-3-yl acetate | 5.926 |
| Cis-3,7-dimethyl-2,6-octadienyl ethanoate | 0.017 |
| 4-methyl-1-propan-2-yl-1-cyclohex-2-enyl acetate | 0.370 |
| Undec-10-enal | 0.037 |
| Undecan-4-olide | 0.044 |
| 4-isopropylbenzaldehyde | 0.052 |
| 2,6,6-trimethylbicyclo[3.1.1]hept-2-ene | 0.236 |
| 2-phenylethanol | 0.148 |
| White wormwood oil (*Artemisia Herba-Alba*) | 0.296 |
| Methyl benzoate | 0.015 |
| 6,6-dimethyl-2-methylenebicyclo[3.1.1]heptane | 1.065 |
| 2,6-di-tert-butyl-p-cresol | 0.185 |
| (Ethoxymethoxy)cyclododecane | 0.074 |
| Endo-1,7,7-trimethyl-bicyclo-[2.2.1]heptan-2-ol | 0.204 |
| 7-methyl-2H-benzo-1,5-dioxepin-3(4H)-one | 0.007 |
| 2,2-dimethyl-3-methylenebicyclo-[2.2.1]-heptane | 0.213 |
| 1,7,7-trimethylbicyclo[2.2.1]-2-heptanone | 0.702 |
| (5R)-2-methyl-5-prop-1-en-2-ylcyclohex-2-en-1-one | 0.185 |
| [1R,(1R*,4E,9S*)]-4,11,11-trimethyl-8-methylene-bicyclo[7.2.0]undec-4-ene | 0.320 |
| extract of lemon tree bark | 0.244 |
| (E)-1-methoxy-4-(1-propenyl)-benzene | 0.370 |
| 3,7-dimethyl-6-octenal | 0.002 |
| 3,7-dimethyl-6-octen-1-ol | 0.006 |
| 2H-1-benzopyran-2-one | 0.407 |
| Mediterranean cypress leaf oil (*Cupressus sempervirens*) | 0.148 |
| 2,6-dimethyloct-7-en-2-ol | 4.815 |
| 3,7-dimethyl-1-octanol | <10 ppm |
| 1-methyl-4-isopropenyl-1-cyclohexene | 0.019 |
| 1,1'-oxydipropan-2-ol | 52.837 |
| 1-methoxy-4-(2-propenyl)-benzene | 0.222 |
| *Eucalyptus globulus* leaf oil | 1.956 |
| 2-methoxy-4-(2-propenyl)-phenol | 0.519 |
| 4,6,6,7,8,8-hexamethyl-1,3,4,6,7,8-hexahydrocyclopenta[g]isochromene | 0.037 |
| 1-methyl-4-isopropyl-1,4-cyclohexadiene | 0.036 |
| 1-methylethyl ester of tetradecanoic acid | 0.036 |
| (2E)-3,7-dimethyl-2,6-octadien-1-ol | <10 ppm |
| *Dipterocarpus turbinatus* oil (*Dipterocarpus turbinatus* balsam oil) | 0.074 |
| 3,7-dimethyl-7-hydroxy-octane-1-al | 0.519 |

TABLE 2-continued

| Designation of the product | % By weight Quantity |
|---|---|
| 6-tert-butylquinoline | 0.089 |
| oil of Hybrid *Lavandula* (*Lavandula Hybrida*) | 0.296 |
| 3,7-dimethyl-2,6-octadienal | 0.137 |
| 2,4-dimethylcyclohex-3-ene-1-carbaldehyde | 0.007 |
| 3,7-dimethyl-octa-1,6-diene-3-ol | 5.613 |
| 4-(4-hydroxy-4-methylpentyl)-3-cyclohexene-1-carboxaldehyde | 0.296 |
| Methyl 2,4-dihydroxy-3,6-dimethylbenzoate | 0.296 |
| 7-methyl-3-methyleneocta-1,6-diene | 0.107 |
| cis-3,7-dimethyl-2,6-octadien-1-ol | 0.016 |
| *Citrus Aurantium Dulcis* bark oil | 1.852 |
| *Citrus Aurantium Dulcis* bark extract | 2.378 |
| Tetrahydro-4-methyl-2-(2-methyl-1-propenyl)-2H-pyrane | 0.296 |
| 1-methyl-4-(1-methylethyl)benzene | 0.071 |
| Patchouli leaf oil (*Pogostemon cablin*) | 1.111 |
| *Rosmarinus officinalis* leaf oil | 0.044 |
| 3-methylbutyl ester of 2-hydroxy-benzoic acid | 0.741 |
| Phenylmethyl ester of 2-hydroxy-benzoic acid | 10.741 |
| 2-hexyl ester of 2-hydroxy-benzoic acid | 0.022 |
| 2-(4-methyl-1-cyclohex-3-enyl)propan-2-ol | 0.072 |
| 4-methyl-1-(1-methylethyl)-3-cyclohexen-1-ol | 0.004 |
| 1-methyl-4-(1-methylethyl)-1,3-cyclohexadiene | 0.150 |
| 5-methyl-2-(1-methylethyl)-phenol | 0.027 |
| 2,4-dimethyl-4-phenyltetrahydrofurane | 0.500 |
| Dihydro-5-pentyl-2(3H)-furanone | 0.500 |

Example 3: Scented Composition No. 3

The masking mixture and the other components of scented composition No. 3, described in table 3, are mixed in order to obtain the scented composition.

TABLE 3

| Designation of the product | % By weight Quantity |
|---|---|
| 1,7,7-trimethyl-bicyclo[2.2.1]heptan-2-ol exo-acetate | 6.667 |
| (5R)-2-methyl-5-prop-1-en-2-ylcyclohex-2-en-1-one | 0.083 |
| *Juniperus virginiana* oil | 0.083 |
| 1,1'-oxydipropan-2-ol | 79.508 |
| *Eucalyptus globulus* leaf oil | 6.667 |
| 2,4-dimethylcyclohex-3-ene-1-carbaldehyde | 0.025 |
| Field mint leaf oil (*Mentha Arvensis*) | 1.667 |
| Spearmint leaf oil (*Mentha viridis*) | 3.333 |
| 2-(4-methyl-1-cyclohex-3-enyl)propan-2-ol | 0.917 |
| Methyl ester of 2-hydroxy-Benzoic acid | 0.050 |
| 2,4-dimethyl-4-phenyltetrahydrofuran | 0.250 |
| Dihydro-5-pentyl-2(3H)-furanone | 0.750 |

Example 4: Scented Composition No. 4

The masking mixture and the other components of scented composition No. 4, described in table 4, are mixed in order to obtain the scented composition.

TABLE 4

| Designation of the product | % By weight Quantity |
|---|---|
| Ethyl ester of acetoacetic acid | 1.500 |
| Isopentyl acetate | 1.500 |
| (Z)-hex-3-enyl acetate | 0.100 |
| Dihydro-5-pentyl-2(3H)-furanone | 0.100 |
| 1,1-dimethyl-2-phenylethyl acetate | 1.500 |
| 3,7-dimethyl-octa-1,6-dien-3-yl acetate | 0.100 |

TABLE 4-continued

| Designation of the product | % By weight Quantity |
|---|---|
| 1-phenylethyl acetate | 0.600 |
| Benzyl alcohol | 0.500 |
| Undecan-4-olide | 3.500 |
| cis-hex-3-en-1-ol; cis-3-hexenol | 0.150 |
| 1-(6-tert-butyl-1,1-dimethyl-2,3-dihydro-1H-inden-4-yl)ethanone | 0.100 |
| 2-propenyl 3-cyclohexanepropanoate | 0.200 |
| 2,6-dimethyloct-7-en-2-ol | 1.000 |
| 2-methyl-1-phenylpropan-2-ol | 0.400 |
| 1,1'-oxydipropan-2-ol | 59.780 |
| 1-(5,6,7,8-tetrahydro-3,5,5,6,8,8-hexamethyl-2-naphthyl)ethan-1-one | 4.500 |
| 4,6,6,7,8,8-hexamethyl-1,3,4,6,7,8-hexahydrocyclopenta[g]isochromene | 1.000 |
| 1,2-diethyl ester of 1,2-benzenedicarboxylic acid | 1.000 |
| 2-propenyl heptanoate | 2.000 |
| Trans-hex-2-enal | 0.150 |
| 4-(2,6,6-trimethylcyclohex-2-enyl)-but-3-ene-2-one | 0.300 |
| 2,4,6-trimethyl-3-cyclohexene-1-carboxaldehyde | 0.600 |
| (Z)-hex-3-enyl 2-methylpropanoate | 0.100 |
| 2-phenoxyethyl 2-methylpropanoate | 5.500 |
| 2-benzylideneheptanal | 0.500 |
| 3,7-dimethyl-2,6-octadienal | 0.100 |
| 2,4-dimethylcyclohex-3-ene-1-carbaldehyde | 0.400 |
| Ethyl ester of 2-methyl-butanoic acid | 0.500 |
| 1,4-dioxacycloheptadecane-5,17-dione | 0.100 |
| *Citrus Aurantium Dulcis* bark extract | 0.100 |
| 2-ethyl-3-hydroxy-4H-pyran-4-one | 0.020 |
| 2-(1,1-dimethylethyl)cyclohexyl acetate | 11.000 |
| 4-tert-butylcyclohexyl acetate | 0.100 |
| 2,4-dimethyl-4-phenyltetrahydrofuran | 0.350 |
| (3E)-4-(2,6,6-trimethylcyclohex-2-en-1-yl)but-3-en-2-one | 0.300 |
| Dihydro-5-pentyl-2(3H)-furanone | 0.350 |

Example 5: Scented Composition No. 5

The masking mixture and the other components of scented composition No. 5, described in table 5, are mixed in order to obtain the scented composition.

TABLE 5

| Designation of the product | % By weight Quantity |
|---|---|
| 2-propenyl ester of (3-methylbutoxy)-acetic acid | 0.688 |
| 3,7-dimethyl-6-octen-1-ol acetate | 0.500 |
| (2E)-3,7-dimethylocta-2,6-dien-1-yl acetate | 0.063 |
| Hexyl acetate | 1.563 |
| Bicyclo[2.2.1]heptan-2-ol-1,7,7-trimethyl exo-acetate | 5.000 |
| 3,7-dimethyl-octa-1,6-dien-3-yl acetate | 3.125 |
| Alpha,alpha,4-trimethylcyclohexylmethyl acetate | 4.375 |
| (4-methyl-1-propan-2-yl-1-cyclohex-2-enyl) acetate | 1.375 |
| Hexan-1-ol | 0.563 |
| Dodecanal | 0.188 |
| Endo-1,7,7-trimethyl-bicyclo-[2.2.1]heptan-2-ol | 0.375 |
| 1,7,7-trimethylbicyclo[2.2.1]-2-heptanone | 2.000 |
| [1R,(1R*,4E,9S*)]-4,11,11-trimethyl-8-methylene-bicyclo[7.2.0]undec-4-ene | 0.125 |
| Texas Cedar oil (*Juniperus Mexicana*) | 6.250 |
| 2H-1-benzopyran-2-one | 1.625 |
| 3a,4,5,6,7,7a-hexahydro-4,7-methanoinden-6-yl acetate | 4.000 |
| 2,6-dimethyloct-7-en-2-ol | 5.250 |
| 1,1'-oxydipropan-2-ol | 43.938 |
| *Eucalyptus globulus* leaf oil | 2.500 |
| oil of Hybrid *Lavandula* (*Lavandula Hybrida*) | 1.250 |
| 3,7-dimethyl-octa-1,6-dien-3-ol | 3.750 |
| Spearmint leaf oil (*Mentha viridis*) | 1.250 |
| (1R,2S,5R)-5-methyl-2-(1-methylethyl)-cyclohexanol | 3.750 |
| Octan-2-one | 0.875 |
| *Rosmarinus officinalis* leaf oil | 0.625 |

TABLE 5-continued

| Designation of the product | % By weight Quantity |
|---|---|
| 4-tert-butylcyclohexyl acetate | 4.000 |
| 2,4-dimethyl-4-phenyltetrahydrofuran | 0.200 |
| (3E)-4-(2,6,6-trimethylcyclohex-2-en-1-yl)but-3-en-2-one | 0.200 |
| Dihydro-5-pentyl-2(3H)-furanone | 0.600 |

Example 6: Scented Composition No. 6

The masking mixture and the other components of scented composition No. 6, described in table 6, are mixed in order to obtain the scented composition.

TABLE 6

| Designation of the product | % By weight Quantity |
|---|---|
| Phenylmethyl ester of acetic acid | 20.000 |
| (Z)-Hex-3-enyl acetate | 0.200 |
| 1-phenylethyl acetate | 0.600 |
| cis-hex-3-en-1-ol; cis-3-hexenol | 0.200 |
| 3,7-dimethyl-6-octen-1-ol | 2.608 |
| 3,7-dimethyl-1-octanol | 0.140 |
| 1,1'-oxydipropan-2-ol | 25.100 |
| (2E)-3,7-dimethyl-2,6-octadien-1-ol | 0.123 |
| 1,3-benzopyrrole | 0.500 |
| 2-benzylideneheptanal | 10.000 |
| 2,4-dimethylcyclohex-3-ene-1-carbaldehyde | 0.400 |
| 2-(4-tert-butylbenzyl)propionaldehyde | 26.000 |
| 3,7-dimethyl-octa-1,6-dien-3-ol | 10.000 |
| cis-3,7-dimethyl-2,6-octadien-1-ol | 0.630 |
| 1,1-dimethoxy-2-phenylethane | 2.500 |
| 2,4-dimethyl-4-phenyltetrahydrofuran | 0.300 |
| Ethyl ester of 10-undecenoic acid | 0.200 |
| (3E)-4-(2,6,6-trimethylcyclohex-2-en-1-yl)but-3-en-2-one | 0.200 |
| Dihydro-5-pentyl-2(3H)-furanone | 0.300 |

Example 7: Test of Reduction of Bad Odours

The scented compositions are tested via sensory analysis in order to prove their masking effectiveness against bad odours. The methods used come from international standards that are applicable in the field of the industries and use olfactory analyses:
  ISO 5492 (Sensory analysis—vocabulary),
  ISO 6658: 2005 (Sensory analysis—Methodology—General guidelines)
  NF V 09-006 (Sensory analysis—Methodology—Initiation and training in detecting and recognising odours),
  ASTM E1958-12 (Standard Guide for Sensory claim substantiation),
  ASTM E1593-13 (Standard Guide for Assessing the efficacy of Air Care products in reducing the perception in indoor malodor).

These sensory analyses allow to define the masking properties, establish a sensory profile and discriminate the scented compositions.

Preparation of the Test

Three bad odours are prepared: toilet, kitchen and tobacco. Thus, three distinct tests are carried out for each of the bad odours.

Bad Toilet Odour:

The compounds that are described in table 7 are mixed and then placed in solution at 10% in alcohol in order to obtain a bad toilet odour.

TABLE 7

| Designation of the product | % by weight |
| --- | --- |
| Skatole | 2.7% |
| B-Thionaphthol | 1% |
| Thioglycolic acid | 21% |
| Caproic acid | 6% |
| P-cresyl phenyl acetate | 1% |
| Isovaleric acid | 2% |
| N-methyl morpholine | 6% |
| Dipropylene glycol | 60.3% |

Bad Kitchen Odour:

The compounds that are described in table 8 are mixed and then placed in solution at 10% in alcohol in order to obtain a bad kitchen odour.

TABLE 8

| Designation of the product | % by weight |
| --- | --- |
| Trimethylamine | 0.1% |
| Methyl sulphide | 0.13% |
| Dimethyldisulphide | 0.02% |
| 2-acetyl pyridine | 3.5% |
| Isovaleric acid | 0.7% |
| Butyric acid | 0.3% |
| Capric acid | 0.5% |
| Methyl amyl ketone | 0.1% |
| Absolute Algae | 2% |
| 2-mercapto propanone | 0.06% |
| Butyl butyrolactate | 1.3% |
| Methional | 0.02% |
| Indole (1% Dipropylene glycol) | 0.14% |
| Diacetyl | 3.5% |
| Caproic acid | 0.2% |
| Guaiacol | 0.04% |
| Oyster base | 0.2% |
| Salmon base | 0.2% |
| Shrimp base | 0.2% |
| Dipropylene glycol | 78.79% |
| Allyl sulphate | 6% |
| Garlic oil mixture | 2% |

Bad Tobacco Odour:

The compounds that are described in table 9 are mixed and then placed in solution at 10% in alcohol in order to obtain a bad tobacco odour.

TABLE 9

| Designation of the product | % by weight |
| --- | --- |
| Furfural | 5 |
| Pyridine | 0.1 |
| Beechwood creosote (Beechwood creosote) | 0.5 |
| Ethyl methyl pyridine | 12.6 |
| Thioglycolic acid | 0.7 |
| Pyroligneous acid | 12 |
| Rectified birch tar essential oil | 30.6 |
| Dipropylene Glycol | 38.5 |

For each test, three samples are prepared:
a first control sample consisting of the bad odour alone,
a second control sample consisting of the scented composition alone, and
a third sample consisting of a mixture of the bad odour and of the scented composition.

The control sample consisting of the scented composition alone is presented on a smelling paper, freely available to the panelists. The concentrated scented products are tested at a level of 0.15 g on a piece of cellulose of 4 cm² that is introduced into a first odourless glass jar having a capacity of 5 L.

The control sample consisting of the bad odour alone is created in the following manner: the bad odour is introduced into a second odourless glass jar having a capacity of 5 L on a piece of cellulose of 4 cm² (80 µg for the bad kitchen odour, 10 µg for the bad toilet odour and 50 µg for the bad tobacco odour).

The sample consisting of a mixture of the bad odour and of the scented composition is created in the following manner:
the bad odour is introduced into a third odourless glass jar having a capacity of 5 L on a piece of cellulose of 4 cm² (80 µg for the bad kitchen odour, 10 µg for the bad toilet odour and 50 µg for the bad tobacco odour).
the concentrated scented products are tested at a level of 0.15 g on a piece of cellulose of 4 cm². This piece of cellulose is disposed next to that of the bad odour.

The jars are coded, randomised and anonymised according to the standard ASTM E1958-12 in order to guarantee a blind test and thus minimise the biases of conscious perceptions of the subject tested. The jars are left 30 min before beginning the evaluation tests in order for the perfume and the bad odour to diffuse.

Evaluation of the Test

The evaluation is carried out by the Expert In-House Panel (Perfumers, Evaluators and Analysts) and comprises on average 15 people. The panel evaluates the scented composition and then fills out a questionnaire in monadic sequential mode, i.e. each expert tests a product A, rates it, then tests a product B, without carrying out a direct conscious comparison. The intensity of the bad odour and the intensity of the perfume of the third sample are thus compared with the two control samples. The intensities are graded on a linear scale from 1 (Very weak) to 10 (very powerful).

Statistical Analysis of the Data:

The statistical processing of the data is carried out with an analysis of the variance (Confidence interval 95%) via the software FIZZ by BIOSYSTEMES.

The products are discriminated using a letter A, B, C etc. in the case of significance and by NC in the case of non-significance.

Results

Use of the Compositions No. 1 and 2

The scented compositions No. 1 and 2, analysed independently in the case of a bad tobacco odour, allowed to reduce the olfactory perception of the bad tobacco odour by 67% and 57%, respectively (see FIG. 1).

Use of the Compositions No. 3 and 4

The scented compositions No. 3 and 4, analysed independently in the case of a bad kitchen odour, allowed to reduce the olfactory perception of the bad kitchen odour by 63% and 60%, respectively (see FIG. 2).

Use of the Compositions No. 5 and 6

The scented compositions No. 5 and 6, analysed independently in the case of a bad toilet odour, allowed to reduce the olfactory perception of the bad toilet odour by 73% and 65%, respectively (see FIG. 3).

The scented compositions studied allow to significantly reduce the perception of the bad toilet, kitchen and tobacco odours. The masking mixture and the scented compositions according to the invention thus allow to mask, in an olfactory manner, the bad odours.

Example 8

The components of table 10 have been mixed in order to obtain comparative masking mixture No. 7.

TABLE 10

| Designation of the product | % By weight |
|---|---|
| 2,4-dimethyl-4-phenyltetrahydrofuran (rhubafuran) | 50 |
| Bicyclononalactone | 50 |

The components of table 11 have been mixed in order to obtain masking mixture No. 8 according to the present invention.

TABLE 11

| Designation of the product | % By weight |
|---|---|
| 2,4-dimethyl-4-phenyltetrahydrofuran (rhubafuran) | 35 |
| Dihydro-5-pentyl-2(3H)-furanone (gamma-nonalactone) | 35 |
| Ethyl ester 10-undecenoic acid (ethyl undecylenate) | 30 |

Example 9

Masking mixture No. 7 (comparative) and the other components of scented composition No. 9 (comparative), described in table 12, are mixed in order to obtain scented composition No. 9 (comparative).

TABLE 12

| Designation of the product | % By weight |
|---|---|
| di-isobutyl carbinyl acetate (Alicate ®) | 16.67 |
| 3-(1,3-benzodioxol-5-yl)-2-methylpropanal (Aquanal ®, Helional ®) | 8.33 |
| 1-(2,3,8,8-tetramethyl-1,2,3,4,5,6,7,8-octahydronaphthalen-2-yl)ethanone (Iso Ambois ®) | 16.67 |
| Oakmoss (moss oakmoss synthetic) | 1.67 |
| Diluent (dipropylene glycol) | 53.32 |
| Masking mixture No 7 (comparative) | 3.34 |

Masking mixture No. 8 and the other components of scented composition No. 10 (comparative), described in table 13, are mixed in order to obtain scented composition No. 10 (comparative).

TABLE 13

| Designation of the product | % By weight |
|---|---|
| di-isobutyl carbinyl acetate (Alicate ®) | 16.67 |
| 3-(1,3-benzodioxol-5-yl)-2-methylpropanal (Aquanal ®, Helional ®) | 8.33 |
| 1-(2,3,8,8-tetramethyl-1,2,3,4,5,6,7,8-octahydronaphthalen-2-yl)ethanone (Iso Ambois ®) | 16.67 |
| Oakmoss (moss oakmoss synthetic) | 1.67 |
| Diluent (dipropylene glycol) | 53.32 |
| Masking mixture No. 8 | 3.34 |

Example 10

Masking mixture No. 7 (comparative) and the other components of scented composition No. 11, described in table 14, are mixed in order to obtain scented composition No. 11.

TABLE 14

| Designation of the product | % By weight |
|---|---|
| (2E)-3,7-dimethylocta-2,6-dien-1-yl acetate | 0.063 |
| [1R,(1R*,4E,9S*)]-4,11,11-trimethyl-8-methylenebicyclo[7.2.0]undec-4-ene | 0.125 |

TABLE 14-continued

| Designation of the product | % By weight |
|---|---|
| Dodecanal | 0.188 |
| Endo-1,7,7-trimethyl-bicyclo-[2.2.1]heptan-2-ol | 0.375 |
| 3,7-dimethyl-6-octen-1-ol acetate | 0.500 |
| Hexan-1-ol | 0.563 |
| Rosmarinus officinalis leaf oil | 0.625 |
| 2-propenyl ester of (3-methylbutoxy)-acetic acid | 0.688 |
| Octan-2-one | 0.875 |
| Hybrid Lavandula oil (Lavandula Hybrida) | 1.250 |
| Spearmint leaf oil (Mentha viridis) | 1.250 |
| (4-methyl-1-propan-2-yl-1-cyclohex-2-enyl) acetate | 1.375 |
| Hexyl acetate | 1.563 |
| 2H-1-benzopyran-2-one | 1.625 |
| 1,7,7-trimethylbicyclo[2.2.1]-2-heptanone | 2.000 |
| Eucalyptus globulus leaf oil | 2.500 |
| 3,7-dimethyl-octa-1,6-dien-3-yl acetate | 3.125 |
| 3,7-dimethyl-octa-1,6-dien-3-ol | 3.750 |
| (1R, 2S, 5R)-5-methyl-2-(1-methylethyl)-cyclohexanol | 3.750 |
| 3a,4,5,6,7,7a-hexahydro-4,7-methanoinden-6-yl acetate | 4.000 |
| 4-tert-butylcyclohexyl acetate | 4.000 |
| Alpha,alpha,4-trimethylcyclohexylmethyl acetate | 4.375 |
| Bicyclo[2.2.1]heptan-2-ol-1,7,7-trimethyl exo-acetate | 5.000 |
| 2,6-dimethyloct-7-en-2-ol | 5.250 |
| Texas Cedar oil (Juniperus Mexicana) | 6.250 |
| 1,1'-oxydipropan-2-ol | 43.935 |
| Masking mixture No 7 (comparative) | 1.000 |

A masking mixture No. 8 and the other components of scented composition No. 12, described in table 15, are mixed in order to obtain scented composition No. 12.

TABLE 15

| Designation of the product | % By weight |
|---|---|
| (2E)-3,7-dimethylocta-2,6-dien-1-yl acetate | 0.063 |
| [1R,(1R*,4E,9S*)]-4,11,11-trimethyl-8-methylenebicyclo[7.2.0]undec-4-ene | 0.125 |
| Dodecanal | 0.188 |
| Endo-1,7,7-trimethyl-bicyclo-[2.2.1]heptan-2-ol | 0.375 |
| 3,7-dimethyl-6-octen-1-ol acetate | 0.500 |
| Hexan-1-ol | 0.563 |
| Rosmarinus officinalis leaf oil | 0.625 |
| 2-propenyl ester of (3-methylbutoxy)-acetic acid | 0.688 |
| Octan-2-one | 0.875 |
| Oil of Hybrid Lavandula (Lavandula Hybrida) | 1.250 |
| Spearmint leaf oil (Mentha viridis) | 1.250 |
| (4-methyl-1-propan-2-yl-1-cyclohex-2-enyl) acetate | 1.375 |
| Hexyl acetate | 1.563 |
| 2H-1-benzopyran-2-one | 1.625 |
| 1,7,7-trimethylbicyclo[2.2.1]-2-heptanone | 2.000 |
| Eucalyptus globulus leaf oil | 2.500 |
| 3,7-dimethyl-octa-1,6-dien-3-yl acetate | 3.125 |
| 3,7-dimethyl-octa-1,6-dien-3-ol | 3.750 |
| (1R,2S,5R)-5-methyl-2-(1-methylethyl)-cyclohexanol | 3.750 |
| 3a,4,5,6,7,7a-hexahydro-4,7-methanoinden-6-yl acetate | 4.000 |
| 4-tert-butylcyclohexyl acetate | 4.000 |
| Alpha,alpha,4-trimethylcyclohexylmethyl acetate | 4.375 |
| Bicyclo[2.2.1]heptan-2-ol-1,7,7-trimethyl exo-acetate | 5.000 |
| 2,6-dimethyloct-7-en-2-ol | 5.250 |
| Texas Cedar oil (Juniperus Mexicana) | 6.250 |
| 1,1'-oxydipropan-2-ol | 43.935 |
| Masking mixture No 8 | 1.000 |

Test of Reduction of the Bad Odours:
Tests Similar to Those of Example 7 were Carried Out.
Results:
Use of the Compositions No. 9 and 12.

The scented composition No. 9 and 12, analysed independently in the case of a bad toilet odour, allowed to reduce the olfactory perception of the bad toilet odour by 44% and 72%, respectively (see FIG. 4). The scented composition according to the present invention (No. 12) is therefore more effective than the comparative scented composition (No. 9).

Use of the Masking Mixtures No. 7 and 8.

The masking mixtures No. 7 and 8, analysed independently in the case of a bad toilet odour, allowed to reduce the olfactory perception of the bad toilet odour by 51% and 54%, respectively (see FIG. 5). The masking mixture according to the present invention containing gamma-nonlactone (No. 8) is therefore more effective than the comparative masking mixture containing bicyclononalactone (No. 7). Gamma-nonalactone thus has better performance than bicyclononalactone.

Use of the Compositions No. 11 and 12.

The scented compositions No. 11 and 12, analysed independently in the case of a bad toilet odour, allowed to reduce the olfactory perception of the bad toilet odour by 63% and 72%, respectively (see FIG. 5).

The scented composition according to the present invention containing gamma-nonalactone (No. 12) is therefore more effective than the scented composition comprising the comparative masking mixture containing bicyclononalactone (No. 11). In a scented composition according to the invention, the addition of the masking mixture containing gamma-nonalactone is therefore more effective that the addition of a masking mixture containing bicyclononalactone. Gamma-nonalactone thus has better performance than bicyclononalactone.

Use of the Scented Compositions No. 9 and 10.

The scented compositions No. 9 and 10, analysed independently in the case of a bad toilet odour, allowed to reduce the olfactory perception of the bad toilet odour by 44% and 50%, respectively (see FIG. 5). In a scented composition of the prior art, the addition of the masking mixture according to the present invention containing gamma-nonalactone (scented composition No. 10) is more effective that the addition of a comparative masking mixture containing bicyclononalactone (scented composition No. 9). Gamma-nonalactone thus has better performance than bicyclononalactone.

Use of the Compositions No. 9 and 12.

The scented compositions No. 9 and 12, analysed independently, show that the scented composition according to the present invention (No. 12) has a perfume intensity significantly greater than the comparative scented composition (No. 9) (see figure No. 6).

Use of the Compositions No. 11 and 12.

The scented compositions No. 11 and 12, analysed independently, show that the scented composition according to the present invention (No. 12) has a perfume intensity significantly greater than the comparative scented composition (No. 11) (see FIG. 6).

The scented compositions according to the present invention allow to significantly reduce the perception of the bad odours tested and have a better effectiveness in comparison to the compositions of the prior art. The masking mixture and the scented compositions according to the invention thus allow to better mask, in an olfactory manner, the bad odours in comparison to the other compositions of the prior art. Further, the effectiveness against the bad odours, the scented compositions according to the invention have better olfactory power (perfume intensity) in comparison to the comparative scented compositions of the prior art.

The invention claimed is:

1. A mixture comprising:
   between 20 and 80 wt % of dihydro-5-pentyl-2(3H)-furanone;
   between 20 and 80 wt % of 2,4-dimethyl-4-phenyltetrahydrofuran; and
   between 20 and 75 wt % of an ethyl ester of 10-undecenoic acid.

2. The mixture according to claim 1, wherein
   the dihydro-5-pentyl-2(3H)-furanone is between 30 and 35 wt % and
   the 2,4-dimethyl-4-phenyltetrahydrofuran is between 30 and 35 wt %.

3. The mixture according to claim 1, further comprising (3E)-4-(2,6,6-trimethylcyclohex-2-en-1-yl)but-3-en-2-one.

4. The mixture according to claim 3, wherein the (3E)-4-(2,6,6-trimethylcyclohex-2-en-1-yl)but-3-en-2-one is between 20 and 75 wt % of the mixture.

5. The mixture according to claim 4, wherein the concentration of ethyl ester of 10-undecenoic acid is between 30 and 35 wt % and the concentration of the (3E)-4-(2,6,6-trimethylcyclohex-2-en-1-yl)but-3-en-2-one is between 30 and 35 wt %.

6. A scented composition comprising the mixture according to claim 1.

7. A cosmetic base comprising the mixture according to claim 1.

8. A detergent base comprising the mixture according to claim 1.

9. A home fragrance comprising the mixture according to claim 1.

10. A method of preparing a scented household product comprising:
    incorporating a quantity of the mixture according to claim 1 into the household product, the household product being selected from a group consisting of a scented composition, cosmetic composition, a detergent base, and a home fragrance.

11. A method for improving unpleasant household odour conditions comprising:
    identifying a first region of the household having an unpleasant odour,
    selecting a household product according to claim 10; and
    distributing the selected household product in at least the first region.

12. The mixture according to claim 2, further comprising (3E)-4-(2,6,6-trimethylcyclohex-2-en-1-yl)but-3-en-2-one.

13. A scented composition comprising the mixture according to claim 2.

14. A scented composition comprising the mixture according to claim 3.

15. A scented composition comprising the mixture according to claim 4.

16. A scented composition comprising the mixture according to claim 5.

17. A cosmetic base comprising the mixture according to claim 2.

18. A cosmetic base comprising the mixture according to claim 3.

19. A cosmetic base comprising the mixture according to claim 4.

20. A cosmetic base comprising the mixture according to claim 5.

* * * * *